United States Patent [19]

Alverson et al.

[11] 4,357,669
[45] Nov. 2, 1982

[54] MONITORING MEANS AND METHOD FOR DETERMINING THE WAX CONTENT OF OIL FROM A SOLVENT DEWAXING UNIT

[75] Inventors: Frederick C. Alverson, Port Arthur; Edward D. MacMurtrie, Port Neches; Norman R. Odell, Nederland, all of Tex.

[73] Assignee: Texaco Inc., White Plains, N.Y.

[21] Appl. No.: 190,122

[22] Filed: Sep. 24, 1980

[51] Int. Cl.³ .............................................. G01N 11/00
[52] U.S. Cl. .................................... 364/500; 364/496; 73/61 R; 196/14.5
[58] Field of Search ............................ 73/61 R, 64, 53; 324/300; 364/496, 500, 497, 501, 552; 208/28, 31, DIG. 1; 196/14.5

[56] References Cited

U.S. PATENT DOCUMENTS

| | | | |
|---|---|---|---|
| 3,549,514 | 12/1970 | Brown et al. | 364/500 X |
| 3,718,809 | 2/1973 | Woodle | 364/500 |
| 3,720,599 | 3/1973 | Gould | 196/14.5 X |
| 3,777,127 | 12/1973 | Goetchius et al. | 364/497 |
| 3,925,721 | 12/1975 | Petroff | 324/300 |
| 3,965,723 | 6/1976 | Harrison | 73/61 R X |
| 3,972,779 | 8/1976 | Harrison | 364/500 X |
| 3,982,422 | 9/1976 | Harrison et al. | 73/61 R X |
| 4,053,744 | 10/1977 | Woodle | 364/501 |
| 4,260,580 | 4/1981 | Sindo et al. | 364/497 X |
| 4,277,832 | 7/1981 | Wong | 364/510 |

*Primary Examiner*—Edward J. Wise
*Attorney, Agent, or Firm*—Carl G. Ries; Robert A. Kulason; Ronald G. Gillespie

[57] ABSTRACT

The output oil from a solvent dewaxing unit is controlled so that it is provided as product oil when the wax content of the output oil is within a predetermined limit, or not provided as product oil when the wax content is not within the predetermined limit. The output oil from the dewaxing unit is sampled and solvent in the sample oil is removed. The solvent-free sample oil is chilled to a predetermined temperature. An analyzer receives the chilled sample oil and provides a signal corresponding to the wax content of the sample oil. A network coupled to the analyzer provides a control signal of one amplitude when the signal from the analyzer is within a predetermined limit and of another amplitude when the signal from the analyzer is not within the predetermined limit. A valve receiving the output oil from the dewaxing unit is responsive to the control signal to provide the output oil as product oil when the control signal is of the one amplitude and does not provide the output oil as product oil when the control signal is of the other amplitude.

12 Claims, 4 Drawing Figures

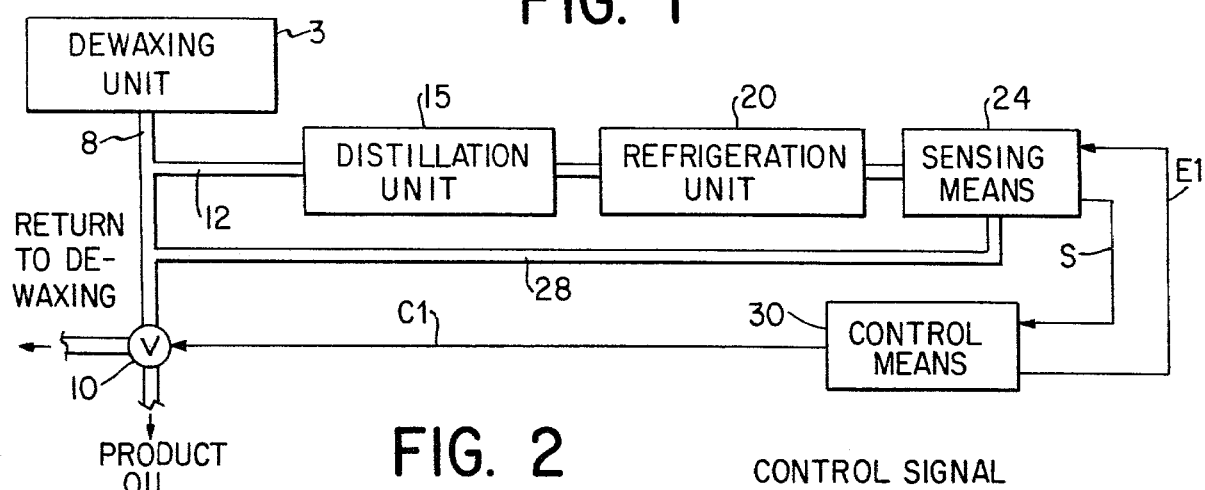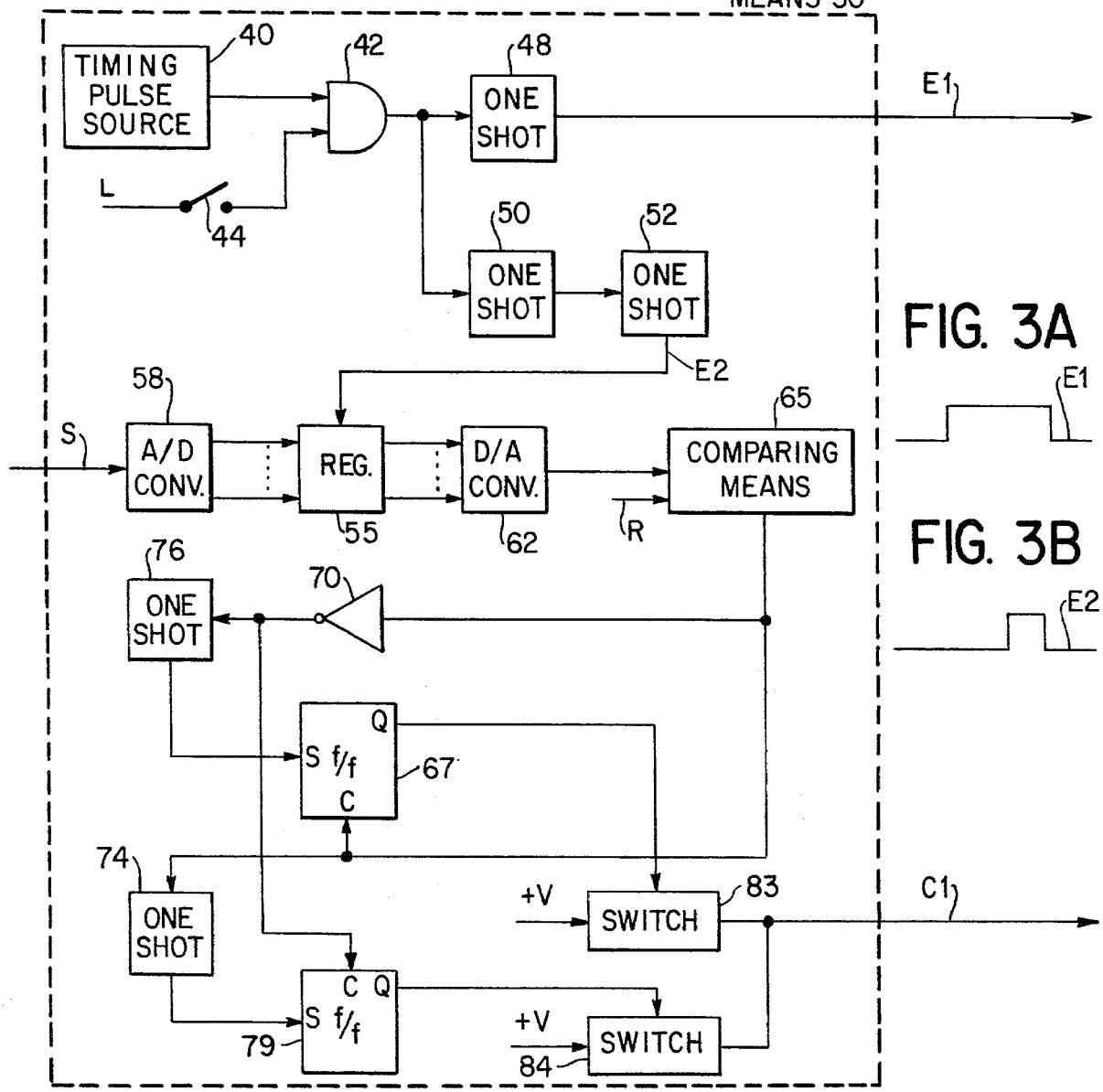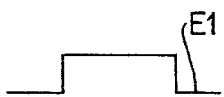

MONITORING MEANS AND METHOD FOR DETERMINING THE WAX CONTENT OF OIL FROM A SOLVENT DEWAXING UNIT

BACKGROUND OF THE INVENTION

Field of the Invention

The present invention relates to monitoring means and methods in general and, more particularly, to monitoring means and methods associated with solvent dewaxing operation.

SUMMARY OF THE INVENTION

A system controls the output oil from a solvent dewaxing unit so that the output oil is provided as product oil when the wax content of the output oil is within a predetermined limit and does not provide the output oil as product oil when the wax content of the output oil is not within the predetermined limit. The system includes apparatus for sampling the output oil and apparatus for removing solvent from the sample oil. The sample oil is then chilled and provided to an analyzer which analyzes the sample oil and provides a signal corresponding to the wax content of the sample oil. A control network coupled to the analyzer provides a control signal of one amplitude when the signal from the analyzer is within a predetermined limit and of another amplitude when the signal from the analyzer is not within the predetermined limit. The output oil from the solvent dewaxing unit is provided to a valve responsive to the control signal from the control network. The valve passes the output oil so as to provide it as product oil when the control signal is of the one amplitude and diverts the output oil so as not to provide it as product oil when the control signal is of the other amplitude.

The objects and advantages of the invention will appear more fully hereinafter, from a consideration of the detailed description which follows, taken together with the accompanying drawings, wherein one embodiment is illustrated by way of example. It is to be expressly understood, however, that the drawings are for illustrative purposes only, and are not to be construed as defining the limits of the invention.

DESCRIPTION OF THE DRAWINGS

FIG. 1 shows a control system, constructed in accordance with the present invention, in partial schematic form and in partial simplified block diagram form, for controlling the output oil from a solvent dewaxing unit.

FIG. 2 is a detailed block diagram of the control signal means shown in FIG. 1.

FIG. 3A and 3B are graphical representations of pulses occurring during operation of the control signal means.

DESCRIPTION OF THE INVENTION

Contamination of product oil by wax is a recurring problem resulting from dewaxing filter failure. Conventional methods for determining the wax content of oil are not very satisfactory. The present invention is a product oil monitor which detects wax contamination of the product oil.

Referring now to FIG. 1, a conventional type dewaxing unit 3 discharges output oil by way of line 8 to valve means 10. Valve means 10, responsive to a control signal C1, provides the output oil as product oil when its wax content is within a predetermined limit. Valve means 10 provides the output oil to storage or for further dewaxing when its wax content is not within the predetermined limit, as hereinafter explained. Another line 12 samples a portion of the output oil and provides sample oil to a distillation unit 15. It should be noted that although the sampling is shown as a continuous stream sampling, discrete sampling may also be used. The details of the specific sampling are not necessary for an understanding of the present invention. Distillation unit 15 removes the dewaxing solvent, thus eliminating solvent interference in the wax content determination. Initially, a gas chromatograph may be used to check for complete removal of solvent. However, once the system is operational and a proper distillation temperature determined, further checks by a gas chromatograph are unnecessary.

Distillation unit 15 provides the sample oil to a refrigeration unit 20. Refrigeration unit 20 cools the sample oil down to a predetermined temperature, preferably between a dewaxing temperature and a pour point temperature, for wax content determination. The prepared sample oil is then provided to sensing means 24 for analysis. Sensing means 24 may include a Newport Analyzer Mark 3, manufactured by Newport Oxford Industries, or its equivalent. Sensing means 24 utilizes low resolution nuclear magnetic resonance to measure wax content in the sample oil. Low resolution nuclear magnetic resonance is affected by hydrogen associated with a liquid, such as oil, but is not affected by hydrogen associated with a solid, such as wax. Therefore, wax-free sample oil will produce a greater signal intensity than wax-containing sample oil. Sensing means 24 provides the sample oil back to line 8 by way of line 28. Sensing means 24 is responsive to pulses E1 from control means 30 to perform the analysis of the sample oil and provides a corresponding signal S to control means 30.

Referring now to FIG. 2, control signal means 30 includes a source 40 of timing pulses. The frequency of the timing pulses determines the frequency of tests. The pulses from source 40 are provided to an AND gate 42. A positive direct current voltage L is applied to a manually operative single pole single throw switch 44. Operation of the system is initiated by an operator who closes switch 44 to pass voltage L which enables AND gate 42 to pass the timing pulses from source 40 to one-shots multivibrators 48 and 50. One-shot 48 provides pules E1, one of which is shown in FIG. 3A. One-shot 50 acts as a time delay and provides pulses to another one-shot multivibrator 52 which provides pulses E2 to a register 55. One of pulses E2 is shown in FIG. 3B. The time delay of one-shot multivibrator 50 is desirable so that the testing by sensing means 24 has sufficient time to stabilize before signal S is accepted as being representative of the test. Signal S is applied to an analog-to-digital converter 58 which converts signal S to corresponding digital signals and provides the digital signals to register 55. Upon occurrence of a pulse E2, register 55 accepts the digital signals from converter 58 and enters them. Register 55 provides digital signals corresponding to its content to a digital-to-analog converter 62, which provides a corresponding analog signal. In effect, converters 58 and 62 cooperate with register 55 to sample and hold signal S each test occurrence. The analog signal from converter 62 is provided to comparing means 65 which also receives a direct current reference signal R corresponding to a maximum acceptable level of wax in the product oil. Comparing means 65 provides an output signal at a high logic level when the wax content of the sample oil is less than the maximum limit and at a low logic level when the wax content of the sample oil is equal to or greater than the maximum limit. The output signal from comparing means 65 is provided to the clear input of a flip-flop 67, to an inverter 70 and to a one-shot multivibrator 74. The output signal from inverter 70 is provided to another one-shot multivibrator 76 and to the clear input of a flip-flop 79. The output signals from one-shots 74, 76 are provided to the set inputs of flip-flop 79 and 67, respectively. The Q outputs of flip-flops 67 and 79 provide signals to electronic single pole, single throw switches 83 and 84, respectively, for controlling the blocking and passing of direct current voltages +V and −V, respectively. The outputs of switches 83 and 84 are tied together so that whichever voltage is passed, it is provided as signal C1.

Normally while the dewaxing unit is providing acceptable product oil, switch 83 is conductive passing +V as signal C1 causing valve means 10 to provide the output oil from dewaxing unit 3 as product oil.

When the wax content of the output oil exceeds the maximum limit, the output signal from comparing means 65 goes to a low logic level, triggering flip-flop 67 to a clear state and triggering one-shot multivibrator 74. A flip-flop provides a high logic level signal at its Q output while in a set state and a low logic level signal at the Q output while in a clear state. The signal from flip-flop 67 goes to a low logic level, causing switch 83 to block the +V voltage. After a suitable time delay determined by the parameters of one-shot 74, the pulse provided by one-shot 74 triggers flip-flop 79 to a set state, so that it provides a high logic level signal to switch 84, causing it to pass the −V voltage as signal C1. When signal C1 is a negative voltage, valve means 10 is actuated to pass the output oil leaving dewaxing unit 3 back to the dewaxing unit for further dewaxing or to a storage tank for storage until further dewaxing.

When the output oil leaving dewaxing unit 3 is again acceptable, the output signal from comparing means 65 goes from a low logic level to a high logic level. Since the output signal from comparing means 65 is inverted by inverter 70, this transition will trigger flip-flop 79 to the clear state and trigger one-shot 76. With flip-flop 79 being in a clear state, the high logic level signal is removed from switch 84 so as to block the −V voltage. After a suitable time delay provided by one-shot 76, flip-flop 67 is triggered to the set state causing it to provide a high logic level signal to switch 83 thereby passing the +V voltage as signal C1 which in turn causes valve means 10 to pass the output oil from dewaxing unit 3 as product oil.

The invention as hereinbefore described is a control system for controlling the output from a dewaxing unit so as to provide it either as product oil or to return it for further dewaxing. The control system includes apparatus for removing solvent in the output oil from the dewaxing unit, apparatus for chilling the sample output oil and sensing apparatus for determining the wax content of the oil from the dewaxing unit.

What is claimed is:

1. A system for controlling the output oil from a solvent dewaxing unit comprising means for sampling the output oil, means for removing solvent from the sample oil, means for chilling the solvent free sample oil, means receiving the chilled sample oil for determining the wax content of the sample oil and providing a signal corresponding thereto, control means coupled to the sensing means for providing a control signal of one amplitude when the signal from the sensing means is within a predetermined limit and of another amplitude when the signal from the sensing means is not within the predetermined limit, and valve means receiving the output oil from the dewaxing unit and responsive to the signal from the control means for providing the output oil as product oil when the wax content of the sample oil is within the predetermined limit and for not providing the output oil as product oil when the wax content of the sample oil is not within limit.

2. A system as described in claim 1 in which the sample oil is chilled to a temperature in the range of between a dewaxing temperature and a pour point temperature.

3. A system as described in claim 2 in which the means for removing solvent from the sample oil heats the sample oil to a temperature sufficient to vaporize the solvent.

4. A system as described in claim 3 in which the sensing means utilizes low resolution nuclear magnetic resonance to sense the wax content of the sample oil.

5. A system as described in claim 4 in which the sensing means is responsive to a pulse signal from the control signal means for periodically sensing the sample oil, and the control signal means includes means for providing the pulse signal, and sample and hold means receiving the signal from the sensing means and the pulse signal from the pulse signal means for sampling and holding the signal from the sensing means during each sensing of the sampling oil to provide a representative signal.

6. A system as described in claim 5 in which the control signal means includes comparing means connected to the sample and hold means and receiving a reference signal corresponding to a predetermined wax content for the product oil for comparing the signal from the sample and hold means with the reference signal and providing a comparison signal corresponding thereto, and switch means receiving a positive direct current voltage and a negative direct current voltage for providing either the positive direct current voltage or the negative direct current voltage as the control signal in accordance with the comparison signal.

7. A method for controlling the output oil from a solvent dewaxing unit comprising the steps of sampling the output oil, removing solvent from the sample oil, chilling the solvent free sample oil, determining the wax content of the sample oil, providing a wax content signal corresponding to the determined wax content, providing a control signal of one amplitude when the wax content signal is within a predetermined limit and of another amplitude when the wax content signal is not within the predetermined limit, providing the output oil as product oil when the wax content of the sample oil is without the predetermined limit, and not providing the output oil as product oil when the waxed content of the sample oil is not within limit.

8. A method as described in claim 7 in which the sample oil is chilled to a temperature in the range of between a dewaxing temperature and a pour point temperature.

9. A method as described in claim 8 in which the step of removing solvent from the sample oil includes heating the sample oil to a temperature sufficient to vaporize the solvent.

10. A method as described in claim 9 in which the sensing step utilizes low resolution nuclear magnetic resonance to sense the wax content of the sample oil.

11. A method as described in claim 10 in which the determining step is done periodically, and the control signal step includes sampling and holding the wax content signal during each determination of the wax content of the sampling oil to provide a signal.

12. A method as described in claim 11 in which the control signal step includes receiving a reference signal corresponding to a predetermined wax content for the product oil, comparing the signal from the sample and hold step with the reference signal, providing a comparison signal corresponding to the comparison, and providing either a positive direct current voltage or a negative direct current voltage as the control signal in accordance with the comparison signal.

* * * * *